United States Patent
Middleman et al.

(10) Patent No.: US 7,169,160 B1
(45) Date of Patent: Jan. 30, 2007

(54) DEVICE FOR ANCHORING TUBULAR ELEMENT

(75) Inventors: Lee M. Middleman, Portola Valley, CA (US); Walter R. Pyka, Redwood City, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/123,614

(22) Filed: Jul. 28, 1998

(51) Int. Cl.
*A61M 29/00* (2006.01)

(52) U.S. Cl. ........................................ 606/191

(58) Field of Classification Search ................ 604/104, 604/96, 101, 106, 107, 264, 528, 105, 96.01, 604/101.01; 600/434, 585; 606/198, 191, 606/200
See application file for complete search history.

(56) References Cited

U.S. PATENT DOCUMENTS

| | | | |
|---|---|---|---|
| 4,043,346 A * | 8/1977 | Mobley et al. | 128/349 R |
| 4,654,028 A * | 3/1987 | Suma | 604/106 |
| 4,832,055 A * | 5/1989 | Palestrant | 128/899 |
| 5,135,517 A | 8/1992 | McCoy | 604/281 |
| 5,152,777 A * | 10/1992 | Goldberg et al. | 606/200 |
| 5,265,606 A | 11/1993 | Kujawski | 128/632 |
| 5,267,960 A * | 12/1993 | Hayman et al. | 604/106 |
| 5,300,086 A * | 4/1994 | Gory et al. | 606/200 |
| 5,334,168 A | 8/1994 | Hemmer | 604/281 |
| 5,353,784 A * | 10/1994 | Nady-Mohamed | 128/20 |
| 5,356,418 A | 10/1994 | Shturman | 606/159 |
| 5,358,496 A * | 10/1994 | Ortiz et al. | 606/198 |
| 5,389,072 A | 2/1995 | Imran | 604/95 |
| 5,391,147 A | 2/1995 | Imran et al. | 604/95 |
| 5,433,723 A * | 7/1995 | Lindenberg et al. | 606/198 |
| 5,456,667 A | 10/1995 | Ham et al. | 604/107 |
| 5,486,183 A | 1/1996 | Middleman et al. | 606/127 |
| 5,492,119 A * | 2/1996 | Abrams et al. | 128/642 |
| 5,509,900 A * | 4/1996 | Kirkman | 604/104 |
| 5,531,685 A | 7/1996 | Hemmer et al. | 604/95 |
| 5,533,967 A | 7/1996 | Imran | 604/95 |

(Continued)

FOREIGN PATENT DOCUMENTS

WO    WO9640325    12/1996

*Primary Examiner*—Cris L. Rodriguez
(74) *Attorney, Agent, or Firm*—Sheldon & Mak PC (57) ABSTRACT

The present invention is directed to an apparatus for anchoring a tubular element, preferably in the form of a catheter, within a passageway formed in a mammalian body, such as in a vessel, artery, duct, channel, or the like. The apparatus comprises a tubular element having a flexible, elongated, hollow tubular outer lumen with a central longitudinal axis extending therethrough, the outer lumen having a proximal end and a distal end. The apparatus further comprises deployment means positioned within the outer lumen and slidable with respect to the outer lumen. The deployment means has a proximal end and a distal end. The apparatus further comprises a plurality of resilient anchoring members preferably formed of a pseudoelastic material. The anchoring members are coupled to the distal end of the deployment means and extend longitudinally beyond the distal end of the deployment means. Each anchoring member is reversibly movable by the deployment means between a first position and a second position. In the first position, at least a portion of each anchoring member is retracted within the outer lumen of the tubular element. In the second position, at least a portion of each of the anchoring members is deployed exteriorly to the outer lumen of the tubular element, so as to engage an inner wall of the mammalian passageway and anchor the tubular element in a selected position within the passageway.

29 Claims, 7 Drawing Sheets

U.S. PATENT DOCUMENTS

| | | | |
|---|---|---|---|
| 5,540,659 A | | 7/1996 | Teirstein .................... 604/104 |
| 5,620,458 A | * | 4/1997 | Green et al. ................ 606/198 |
| 5,649,953 A | * | 7/1997 | Lefebvre .................... 606/200 |
| 5,653,684 A | * | 8/1997 | Laptewicz et al. ............ 604/22 |
| 5,681,347 A | * | 10/1997 | Cathcart et al. ............ 606/200 |
| 5,713,853 A | * | 2/1998 | Clark et al. .................. 604/53 |
| 5,800,394 A | * | 9/1998 | Yoon et al. .................. 604/101 |
| 5,853,420 A | * | 12/1998 | Chevillon et al. ........... 606/200 |
| 5,855,565 A | * | 1/1999 | Bar-Cohen et al. .......... 604/104 |
| 5,885,258 A | * | 3/1999 | Sachdeva et al. ............ 604/281 |
| 5,904,670 A | * | 5/1999 | Schreiner .................... 604/280 |
| 5,910,144 A | * | 6/1999 | Hayashi ...................... 606/108 |
| 5,911,734 A | * | 6/1999 | Tsugita et al. .............. 606/200 |
| 5,928,260 A | * | 7/1999 | Chin et al. .................... 606/200 |
| 5,938,683 A | * | 8/1999 | Lefebvre .................... 606/200 |
| 5,944,728 A | * | 8/1999 | Bates ........................ 606/127 |
| 5,951,567 A | * | 9/1999 | Javier, Jr. et al. ........... 606/198 |
| 5,968,064 A | * | 10/1999 | Selmon et al. .............. 606/189 |
| 6,027,460 A | * | 2/2000 | Shturman .................... 600/585 |
| 6,027,518 A | * | 2/2000 | Gaber ........................ 606/198 |
| 6,071,263 A | * | 6/2000 | Kirkman .................... 604/104 |
| 6,152,946 A | * | 11/2000 | Broome et al. ............. 606/200 |

* cited by examiner

DEVICE FOR ANCHORING TUBULAR ELEMENT

BACKGROUND

The present invention relates to an apparatus for anchoring a tubular element such as a catheter within a passageway in a mammalian body. In particular, the present invention relates to an anchoring device provided within a catheter that is operable to position and retain the tubular element in place within vessels, arteries, ducts, and channels within the mammalian body.

In various medical procedures in which a catheter is inserted into tubular shaped structures in the body, such as vessels, arteries, ducts, and channels, it is important to anchor the catheter for specific periods of time at a selected location. For example, a common medical procedure that utilizes catheters involves the measuring of certain characteristics of a patient's blood and the monitoring of the patient's blood on a continuous basis. Continuous monitoring is desirable to obtain real time monitoring of the patient's condition. Typically, various intravascular blood gas sensing devices are used to measure blood gas concentrations, including concentrations of oxygen, carbon dioxide, pH level, and the like. However, a challenging problem in the use of blood gas sensors is the difficulty in retaining the catheter in place within the vessel and the difficulty in stabilizing the blood gas sensors so as to obtain an accurate flow reading. For example, due to movement of the sensors, attempts to measure blood gas concentrations directly and continuously have resulted in inaccurate and erratic sensor values.

In addition, the difficulty in anchoring or retaining tubular elements in place within a body passageway, such as a blood vessel, also affects their use with translumenal ultrasonic sensors which can be used to obtain images of blood vessels. For example, it is important to minimize the movement of translumenal ultrasonic sensors within a body passageway such as a blood vessel in order to obtain high quality images of the blood vessel. Moreover, the difficulty in anchoring or retaining tubular elements in place within a body passageway may also affect their use with drug delivery systems, drug dosing, ultrasound systems, and sampling of a body material or fluid.

Devices for positioning tubular elements such as catheters within the body are known. However, many of these devices are not designed to be reversibly removed or moved to another location, and many of these devices are not designed to position or anchor a catheter over a very short distance, i.e., less than 1 centimeter.

There are known devices for positioning a sensor device in an artery, as exemplified in U.S. Pat. No. 5,265,606 to Kujawski. The disclosed device includes an introducer catheter formed in a zigzag pattern having successive bends alternating on opposite sides of the central axis of the catheter, such that when the catheter is placed in the patient's artery, the bends on the opposite sides of the central axis will engage the wall of the artery lumen thus tending to stabilize the catheter in the lumen. However, the device is not designed to anchor the catheter over a very short distance, as the device includes a probe constructed to be passed through the catheter shaft, and the distal end of the probe protrudes substantially beyond the distal outlet. Moreover, in certain embodiments, the tip of the probe may be pointed which creates the danger of puncturing the vessel wall.

Other known devices, such as disclosed in U.S. Pat. No. 5,135,517 to McCoy, include at least two separate positioning elements comprised of shape memory alloys and used to position a core member within a passageway formed in a body. However, the device uses a power supply to activate the thermal shape memory metal. Use of a power supply increases the complexity and the cost. In addition, if the power supply in McCoy is turned off, the device does not necessarily contract back to its original shape by itself. Moreover, there is a danger of overheating the device, and there is the time inconvenience of having to wait for the device to cool down so that it can be safely removed from the body without injury to vessels.

Thus, there is a need for a device that anchors or positions a tubular element such as a catheter in body passageways, such as vessels, arteries, ducts, and channels. In particular, there is a need for a device that is designed to be reversibly removable from one selected location to another and that is designed to anchor or position a catheter over a very short distance, i.e., less than 1 centimeter, and that is designed to aid in accurately positioning a catheter in body passageways. In addition, there is a need for a device that anchors or positions a catheter in place within a body passageway and stabilizes intravascular blood gas sensors ($O_2$, $CO_2$, pH, and the like), so as to obtain accurate flow readings or sensor values. Moreover, there is a need for a device that anchors or positions a catheter in place within a body passageway and that minimizes the movement of translumenal ultrasonic sensors in the body passageway, so as to obtain high quality images of the body passageway such as blood vessels, etc., and that also minimizes movement of tubular components used in drug delivery systems, ultrasound systems, and body sampling systems. There is also a need for a device that may comprise a pseudoelastic shape memory alloy material and that includes all of the advantages that such a material provides. Finally, there is a need for a device that is easy to manufacture and assemble, that requires no power supply, requires no external heating or body heating or cooling down, and that minimizes the potential for tissue damage or discomfort to a patient upon insertion, deployment, and removal of the device.

SUMMARY OF THE INVENTION

The present invention is directed to an apparatus for anchoring a tubular element such as a catheter within a passageway formed in a mammalian body, such as in a vessel, artery, duct, channel, or the like. The apparatus is particularly suitable for anchoring and retaining steerable catheters within blood vessels, stabilizing blood flow sensors accurately in the center of a blood vessel to obtain an accurate flow or sensor reading, minimizing the movement of translumenal ultrasonic sensors to obtain high quality images, and minimizing the movement of tubular components used in connection with drug delivery systems, ultrasound systems, and body sampling systems. In addition, the apparatus of the present invention is easy to manufacture and assemble, requires no power supply, requires no heating or cooling down, and minimizes the potential for tissue damage or discomfort to a patient upon insertion, deployment and removal of the device.

The present invention provides an apparatus for anchoring a tubular element within a passageway formed in a mammalian body. According to one aspect of the present invention, the apparatus comprises a tubular element, preferably a catheter, having a flexible, elongated, hollow tubular outer lumen with a central longitudinal axis extending therethrough. The outer lumen has a proximal end and a distal end. The apparatus further comprises deployment means positioned within the outer lumen and slidable with respect to the outer lumen. The deployment means has a proximal end and a distal end. The apparatus further comprises a plurality of resilient anchoring members coupled to the distal end of the deployment means and extending longitudinally beyond the distal end of the deployment means. Each anchoring member is reversibly movable by the deployment means between a first position and a second position. In the first position, at least a portion of each anchoring member is retracted within the outer lumen of the tubular element. In the second position, at least a portion of each anchoring member is deployed exteriorly to the outer lumen of the tubular element, so as to engage an inner wall of the mammalian passageway and anchor the tubular element in a selected position within the passageway.

According to another aspect of the present invention, the outer lumen of the tubular element may also include openings near the distal end of the outer lumen through which at least a portion of each anchoring member may be deployed so as to engage an inner wall of a mammalian passageway and anchor the tubular element in a selected position within the passageway.

According to the present invention, the deployment means may comprise a flexible, elongated, hollow tubular inner lumen. The deployment means may also comprise a flexible, elongated, hollow tubular inner lumen having a movable guide wire positioned within the inner lumen, wherein the guide wire has a proximal end and a distal end, and the distal end of the guide wire is coupled to a cap member, and the cap member is further coupled to the anchoring members. The deployment means may also comprise a guide wire having a proximal end and a distal end and further having a collar member coupled to the distal end of the guide wire.

Preferably, the anchoring members are comprised of a pseudoelastic material such as a nickel titanium alloy. However, the anchoring members may also be comprised of a material such as spring steel. Preferably, the number of anchoring members is two, three or four. Each of the anchoring members comprises a first end portion and a second end portion. Preferably, the first end portion of each of the anchoring members is coupled to the distal end of the deployment means. In one version, the second end portions of each of the anchoring members may be coupled to a cap member. In another version, the second end portions of each of the anchoring members may be coupled to a retaining ring.

The present invention also provides a method for anchoring a tubular element within a passageway formed in a mammalian body. The method comprises the steps of, providing the anchoring apparatus of the present invention in the various embodiments, positioning the apparatus at a selected location within the passageway, deploying at least a portion of the anchoring members of the apparatus against an inner wall within the passageway, and disengaging the anchoring members from the inner wall and retracting the anchoring members back into the tubular element.

DESCRIPTION OF THE DRAWINGS

These and other features, aspects, and advantages of the present invention will become better understood from the following description, appended claims, and accompanying drawings where:

DETAILED DESCRIPTION OF THE INVENTION

The present invention is directed to, an apparatus for anchoring a tubular element such as a catheter within a passageway formed in a mammalian body, such as in a vessel, artery, duct, channel, or the like. The apparatus is particularly suitable for anchoring and retaining steerable catheters within blood vessels, stabilizing blood flow sensors accurately within a blood vessel to obtain an accurate flow or sensor reading, minimizing the movement of translumenal ultrasonic sensors to obtain high quality images, and minimizing the movement of tubular components used in connection with drug delivery systems, ultrasound systems, and body sampling systems. Moreover, the apparatus is particularly suitable for minimizing the potential for tissue damage or discomfort to a patient upon insertion, deployment, and removal of the apparatus.

Figure 1:
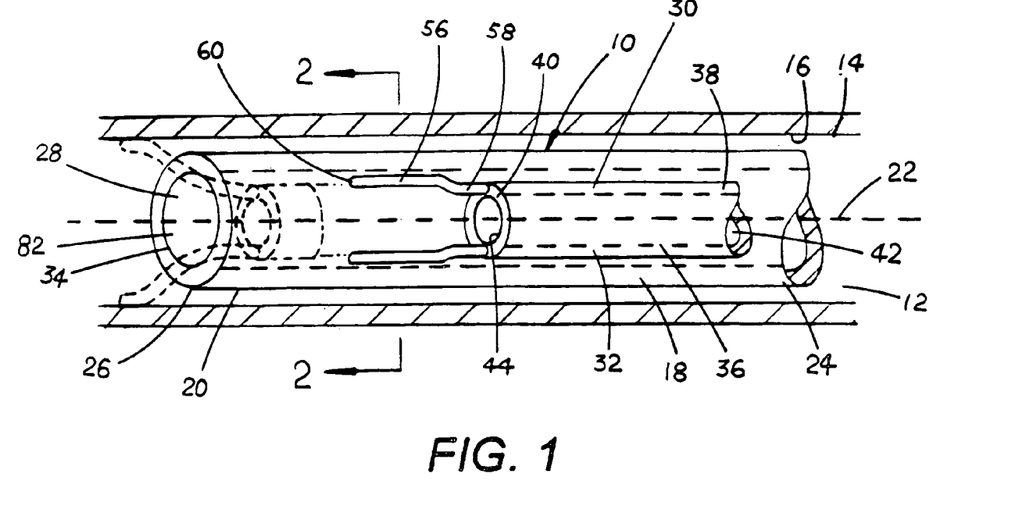
FIG. 1 shows a side view of a first embodiment of the device of the present invention positioned within a body passageway with the anchoring members in a retracted position, and also showing in phantom the anchoring members being deployed.

FIGS. 1–9 show a first embodiment of the present invention including variations of certain features. FIG. 1 shows a side view of the first embodiment of the present invention wherein an anchoring apparatus 10 is positioned within a mammalian passageway 12 defined by an inner wall 14 having a first surface 16. Typically, the mammalian passageway may be a blood vessel, artery, duct or channel. The apparatus 10 comprises a tubular element 18 having a flexible, elongated, hollow tubular outer lumen 20 with a central longitudinal axis 22 extending therethrough. The outer lumen has a proximal end 24 and a distal end 26, and an elongated bore 28 which extends between the proximal end 24 and the distal end 26. Preferably the outer lumen 20 is substantially centered within the mammalian passageway, i.e., vessel, artery, etc., with the central longitudinal axis 22 being disposed along the central longitudinal axis (not shown) of the body passageway. Preferably, the tubular element 18 is in the form of a catheter or other device configured to be maneuvered through body passageways. Preferably, the tubular element 18 is capable of bending during advancement of the apparatus 10 in body passageways to enable varied positioning and placement of the apparatus 10. The tubular element 18 may be formed of a flexible polymeric material, such as polyethylene, polypropylene, or other suitable polymeric materials. The outer diameter of the outer lumen 20 varies depending on the size of the passageway in which the apparatus 10 is used. Typically, the outer lumen 20 has an outer diameter D1 in the range of about 1.0 mm (millimeters) to about 7.0 mm.

As shown in FIG. 1, the apparatus 10 further comprises deployment means 30 positioned within the outer lumen 20. The deployment means 30 may have varying configurations, all of the configurations having a proximal end and a distal end. An outer surface 32 of the deployment means 30 is slidably movable with respect to an inner surface 34 of the outer lumen 20.

As shown in FIGS. 1–4, in one variation of the deployment means 30, the deployment means 30 comprises a flexible, elongated, hollow tubular inner lumen 36 having a proximal end 38, a distal end 40, and an elongated bore 42 which extends between the proximal end 38 and the distal end 40. The inner lumen also has an inner wall 44. Because the inner lumen 36 is hollow, this enables liquids to be transported through the inner lumen to the passageway site. In addition, it enables devices, such as a transducer, to be inserted and used at the site. Preferably, the inner lumen 36 is substantially centered within the outer lumen 20 along the central longitudinal axis 22 of the outer lumen 20. The inner lumen 36 may be formed of a flexible polymeric material, such as polyethylene, polypropylene, or other suitable polymeric materials, or may be formed of a suitable metal. Typically, the inner lumen 36 has an outer diameter D2 in the range of about 0.7 mm (millimeters) to about 6.0 mm, the diameter D2 being sized and selected so that it is slidable within the selected outer lumen 20.

Figure 5:
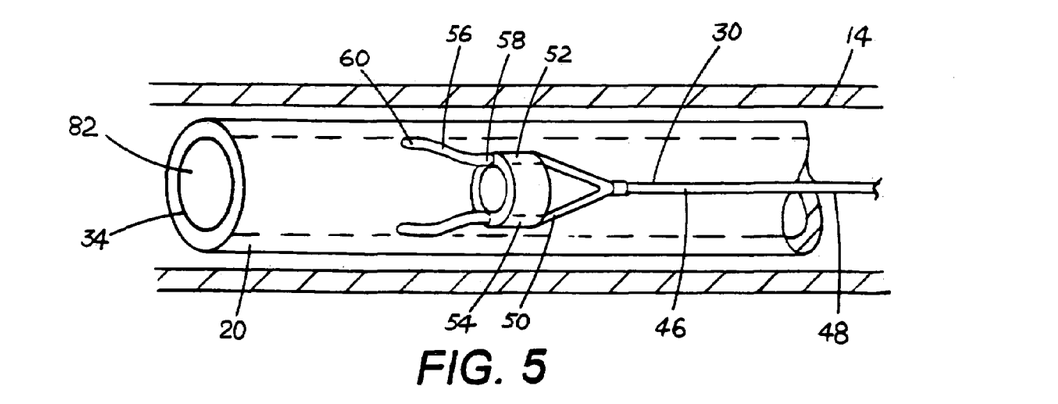
FIG. 5 shows a variation of the deployment means of the first embodiment of the device of the present invention wherein the deployment means comprises a guide wire coupled to a collar member.

As shown in FIG. 5, in another variation of the deployment means 30, the deployment means 30 may comprise a flexible, elongated guide wire 46 having a proximal end 48 and a distal end 50 wherein the distal end 50 of the guide wire 46 is coupled to or attached to a collar member 52. The distal end 50 of the guide wire 46 may be V-shaped. Preferably, the guide wire is comprised of a suitable flexible metal or polymeric material. Preferably, the collar member 52 is comprised of a suitable polymeric material. The collar member 52 should be of a suitable length so as to allow an outer surface 54 of the collar member 52 to be slidably movable with respect to the inner surface 34 of the outer lumen 20, and so the collar member 52 does not get unnecessarily angled or wedged within the outer lumen 20.

Figure 8:
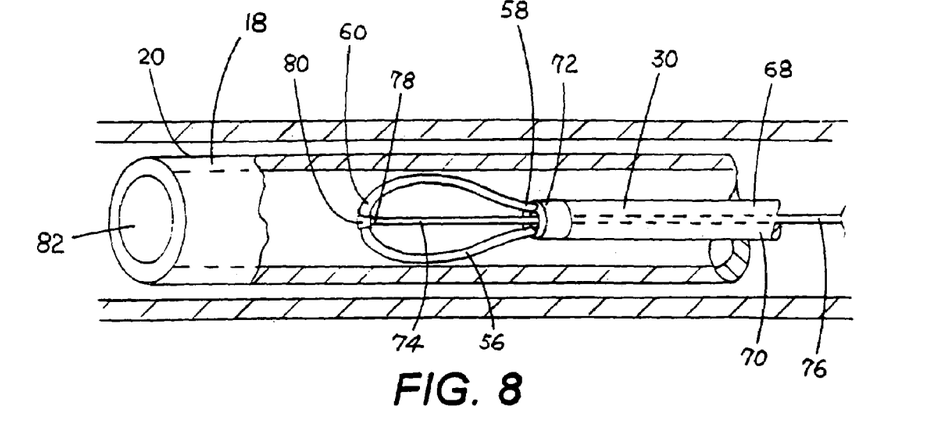
FIG. 8 shows a variation of the deployment means and anchoring members of the first embodiment of the device of the present invention wherein the deployment means comprises an inner lumen having a guide wire coupled to the anchoring members, and the anchoring members are in a retracted position.
Figure 9:
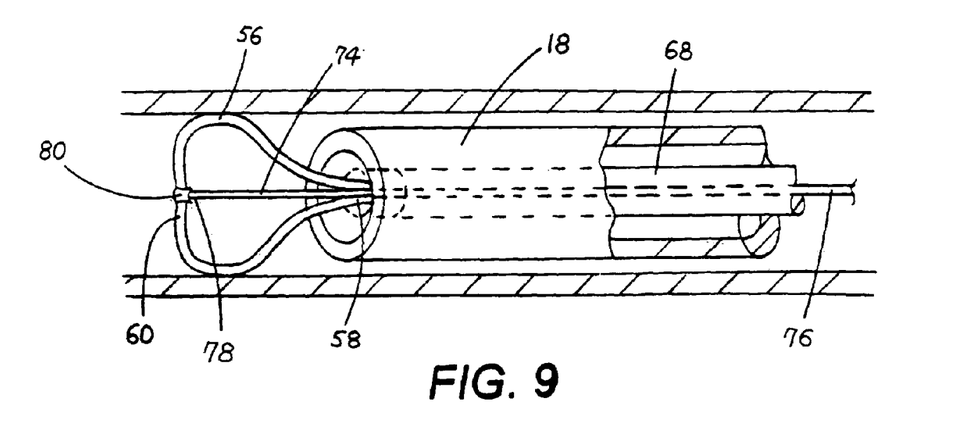
FIG. 9 shows a variation of the deployment means and anchoring members of the first embodiment of the device of the present invention wherein the deployment means comprises an inner lumen having a guide wire coupled to the anchoring members, and the anchoring members are in a deployed position.

As shown in FIGS. 8–9, another variation of the deployment means 30 is shown, and will be discussed in further detail in connection with the discussion of FIGS. 8–9 below.

As shown in FIG. 1 and other FIGS., the apparatus 10 further comprises a plurality of resilient anchoring members 56 coupled to the distal end of the deployment means 30 and extending longitudinally beyond the distal end of the deployment means 30. The anchoring members 56 are designed to anchor or position the tubular element 18 or catheter in place within a mammalian passageway. As shown in FIG. 1, the anchoring members are shown in a retracted position, and are also shown in phantom being deployed.

Preferably, the anchoring members 56 of the present invention are comprised of an elastic material, and in particular, a pseudoelastic material, such as a nickel titanium (NiTi) alloy. Other suitable pseudoelastic materials may include for example, binary nickel titanium, and nickel titanium containing alloys including elemental additions such as V, Fe, Nb, Co, and Zr. Other suitable pseudoelastic materials include copper-based alloys comprising Cu, Al, and Zn; Cu, Al and Ni; and Cu and Zn.

The term "elastic material" as used herein means a material that has spring-like properties, that is, it is capable of being deformed by an applied stress and then springing back or recovering to or toward its original unstressed shape or configuration when the stress is removed. The elastic material is preferably highly elastic. The material can be polymeric or metallic, or a combination of both. The use of metals such as shape memory alloys is preferred. Shape memory alloys that exhibit pseudoelasticity, in particular, superelasticity, are especially preferred. U.S. Pat. No. 4,935,068 to Duerig teaches the fundamental principles of shape memory alloys, and is herein incorporated by reference. U.S. Pat. No. 5,486,183 to Middleman et al. also includes a discussion of pseudoelasticity, and is herein incorporated by reference.

A pseudoelastic alloy is capable of being elastically deformed far beyond the elastic limits of conventional metals. When a shape memory alloy is used, it is preferably a nickel titanium based alloy, which may include additional elements which might affect the yield strength that is available from the alloy or the temperature at which particular desired pseudoelastic characteristics are obtained. It is believed that the superelastic property is achieved by phase transformation within the alloy, rather than by the dislocation movements which occur during the plastic deformation of ordinary metals. Shape memory alloys have a special feature which is beneficial for certain of the embodiments of the present invention.

The use of nickel titanium alloy in the manufacture of the anchoring members 56 provides several advantages. The use of a nickel titanium alloy ensures a force no greater than a predetermined value because of the non-linear nature of nickel titanium based alloy. Thus, even though vessel size may vary, the maximum force will not exceed a given value. As a superelastic shape memory alloy is increasingly deformed from its unconstrained shape, some of its austenitic phase changes into stress-induced martensite. A stress/strain curve presents a plateau during this phase change. This means that while the alloy undergoes this phase change, it can deform greatly with only minimal increases in loading. Therefore, elements comprising superelastic shape memory alloys have a built-in safety feature. Just as the stress/strain curves of shape memory alloys present a plateau upon loading, they also present a plateau in the stress/strain curve upon unloading. Unloading occurs when an element made of superelastic shape memory alloy is permitted to revert from a significantly deformed shape toward its original unstressed shape. Because of the plateau, such an element can maintain an almost constant force during much of the unloading cycle until just before it is completely unloaded.

Figure 4:
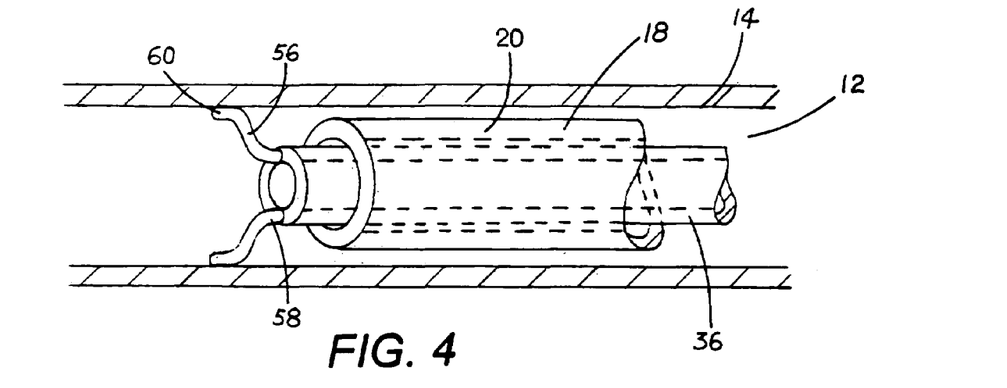
FIG. 4 shows a side view of the first embodiment of the device of the present invention positioned within a body passageway with the anchoring members in a deployed position at a very short distance exterior to the tubular element.

Another advantage in using a nickel titanium alloy in the manufacture of the anchoring members 56 is that a maximum force for a given deflection is provided because a material of thick cross-section can be used given the 4% to 8% deformation possible. In addition, the use of a nickel titanium alloy allows for a more dramatic change for anchoring in a short distance. For example, as shown in FIG. 4, the use of nickel titanium alloy allows the anchoring of the tubular element 18 within the mammalian passageway 12 by deployment of the anchoring members 56 over a very short distance and adjacent the inner wall 14 of the mammalian passageway 12. The distance may be in the range of less than 1 centimeter. Preferably, the distance is less than 5 mm (millimeters). Most preferably, the distance is 1 mm to 3 mm.

The use of pseudoelastic material for the anchoring members of the present invention may prevent excess force on the wall of the mammalian passageway due to the nature of the stress-strain plateau. After the pseudoelastic material is deformed a certain amount (strain), the force does not continue to increase.

In addition to the use of a pseudoelastic material for the anchoring members 56, the anchoring members 56 may also be comprised of a material such as spring steel or other suitable spring material. However, although spring steel is less expensive to use, it does not provide the same amount of constant force or change over a short distance as does a pseudoelastic material. When used in the anchoring apparatus of the present invention, neither the pseudoelastic material nor the spring steel require external heating, such as by an external heating device, or require heating by the body, and also do not require external cooling devices.

Preferably, the number of anchoring members in the device of the present invention is two, three, or four. An apparatus of the present invention having two anchoring members is easier to manufacture, and an apparatus of the present invention having four anchoring members adds greater stability. However, an apparatus of the present invention having three anchoring members is most preferred because the ability to position and anchor the tubular element is maximized. However, it is also contemplated that a greater number of anchoring members may also be used in the present invention.

Figure 16:
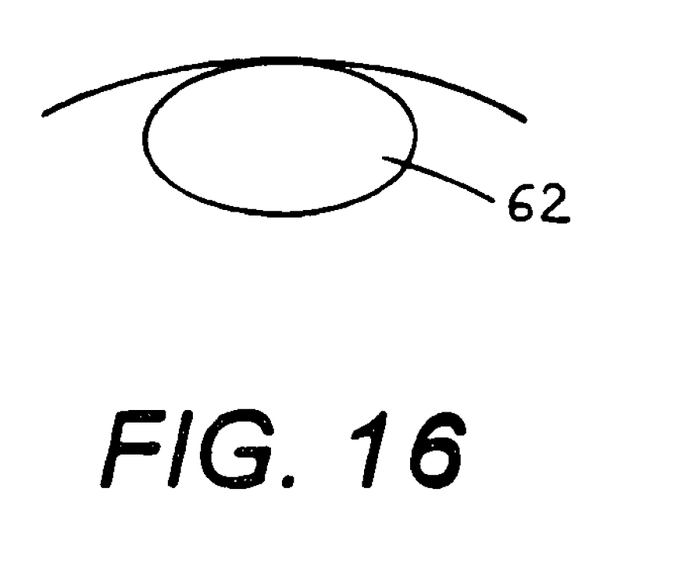
FIG. 16 shows a cross-sectional view of a distal end of an anchoring member deployed against the wall of a passageway; and, FIG. 17 shows a cross-sectional view of another version of a distal end of an anchoring member of the present invention deployed against the wall of a passageway.
Figure 17:
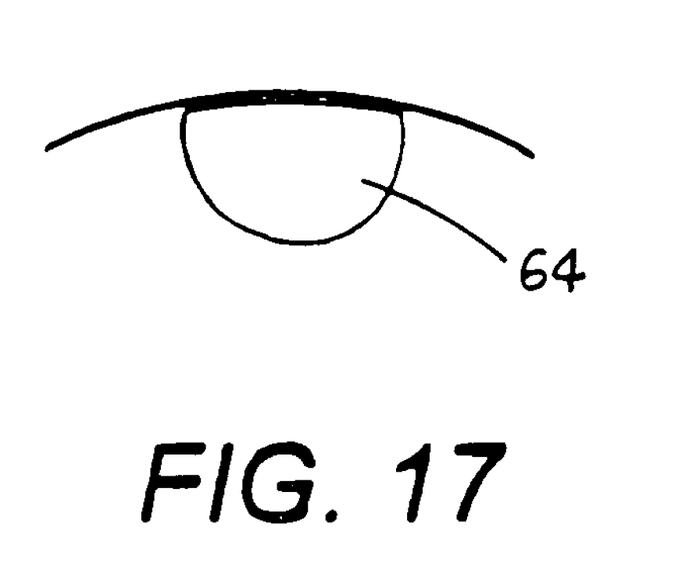

Preferably, the anchoring members 56 are spaced apart from each other and spaced equidistance from each other about the circumference of the deployment means 30, both when retracted within the outer lumen 20 or deployed from the outer lumen 20. As shown in FIG. 1, each anchoring member 56 has a first end portion 58 coupled to the distal end of the deployment means and a second end portion 60. The shape of the anchoring members, especially the second end portion, may vary depending on the amount of contact that is desired by the anchoring members against the passageway surface and depending on the curvature of the passageway surface. For example, the anchoring members may be designed to have a substantially oval cross-section 62, as shown in FIG. 16, to provide a greater surface area of contact when the anchoring member is in contact with the inner wall of the passageway. Further, the anchoring members may be designed to have a cross-sectional shape 64, as shown in FIG. 17, wherein the top portion in contact with the passageway is substantially flat to provide an even greater surface area of contact when the anchoring member is in contact with the inner wall of the passageway. It is desirable that the anchoring members, especially the second end portion of the anchoring members, be designed to provide a greater surface area of contact against the passageway, which, in turn, provides a greater anchoring force.

Preferably, the anchoring members are constructed to have a slight bend, so that when they are deployed from the outer lumen, the anchoring members bow outwardly with a spring-like motion against the inner wall of the passageway. Typically, each anchoring member has a length in the range of about 1.0 mm (millimeter) to about 10.0 mm and a diameter D3 in the range of about 0.2 mm to about 1.0 mm, depending on the size of the selected lumen.

Typically, the anchoring members are first manufactured as separate structures rather than as a unitary structure with the other components of the apparatus 10, and then they are assembled together. The anchoring members may be attached to the deployment means by various methods known in the art, depending on what material the anchoring members and deployment means are comprised of. If the anchoring members are comprised of a pseudoelastic material, such as nickel titanium, the anchoring members may be attached to the deployment means by welding or by soldering with tin-silver or tin-gold, and using an aggressive flux. In addition, the anchoring members may be press-fit, crimped, or swedged to create attachment to the deployment means. In addition, attachment with an epoxy may also be used. Occasionally, for low stress applications, the pseudoelastic material may be laser welded, followed by a post-weld heat treatment to relieve stress at the joint. If the anchoring members are comprised of a spring steel material, the anchoring members may be attached to the deployment means by welding or by soldering.

Figure 2A:
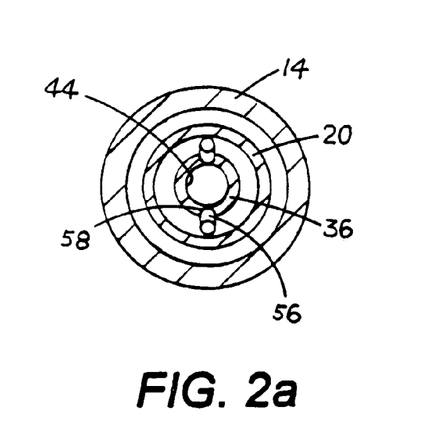
FIG. 2a shows an enlarged transverse cross-sectional view taken along lines 2—2 of FIG. 1, wherein the anchoring members are mounted within the wall of the inner lumen.
Figure 2B:
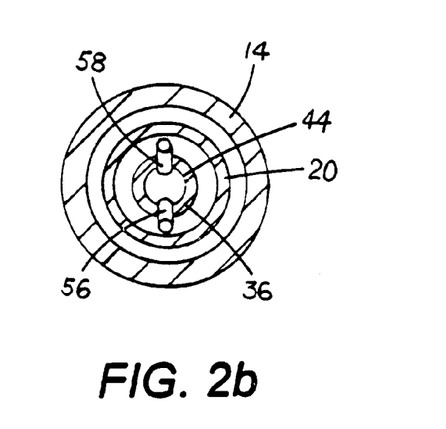
FIG. 2b shows an alternate variation of the enlarged transverse cross-sectional view of FIG. 2a, wherein the anchoring members are attached to the inner wall of the inner lumen.
Figure 3:
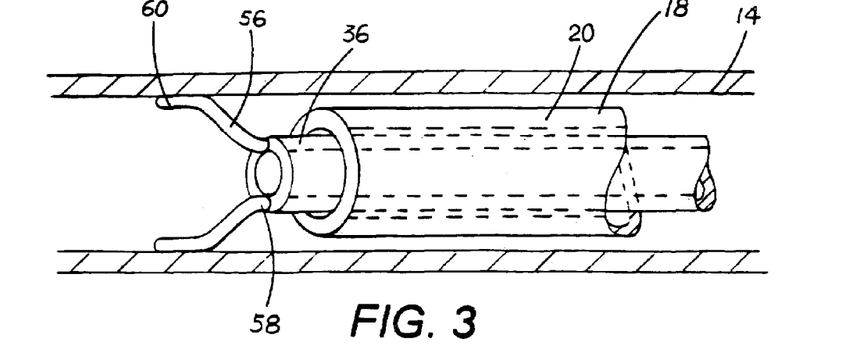
FIG. 3 shows a side view of the first embodiment of the device of the present invention positioned within a body passageway with the anchoring members in a deployed position.

If the inner lumen 36 is made of a polymeric material, the anchoring members may be attached to the deployment means by mounting the anchoring members within the wall of the deployment means. FIG. 2a shows an enlarged cross-sectional view taken along lines 2—2 of FIG. 1, wherein the first end portions 58 of the anchoring members 56 are mounted within the inner wall 44 of the inner lumen 36 at the distal end 40 of the inner lumen 36. This type of attachment of the anchoring members provides a strong and stable attachment. FIG. 2b shows an alternate variation of the enlarged transverse cross-sectional view of FIG. 2a, wherein the first end portions 58 of the anchoring members 56 are coupled to the surface of the inner wall 44 of the inner lumen 36 at the distal end 40 of the inner lumen 36.

Figure 6:
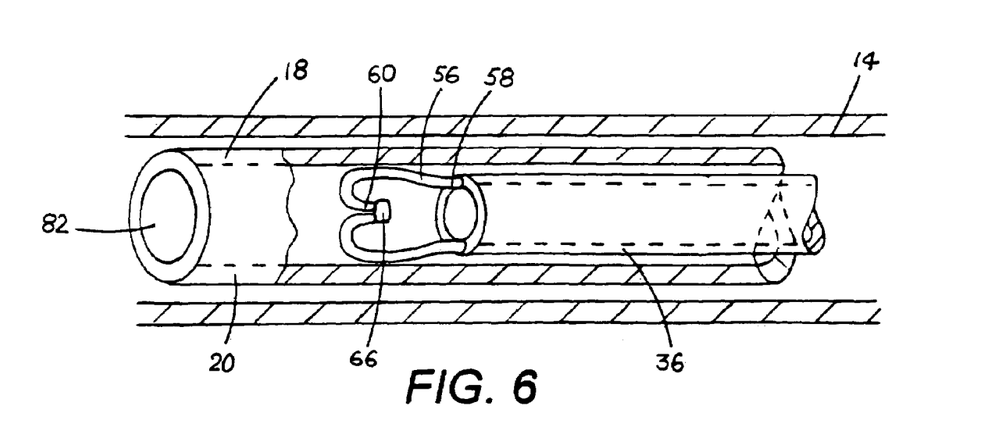
FIG. 6 shows a variation of the anchoring members of the first embodiment of the device of the present invention wherein the anchoring members are coupled to a cap member and are in a retracted position.
Figure 7:
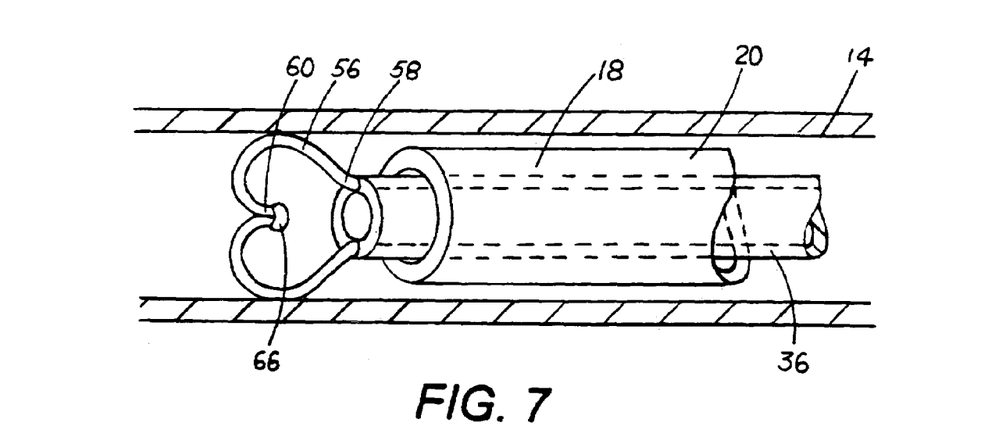
FIG. 7 shows a variation of the anchoring members of the first embodiment of the device of the present invention wherein the anchoring members are coupled to a cap member and are in a deployed position.

As shown in FIGS. 6–7, a variation of the configuration of the anchoring members 56 is shown. The second end portions 60 of the anchoring members 56 are curved inwardly toward each other and coupled to a cap member 66. Preferably, the cap member 66 is comprised of a suitable polymeric material or suitable metal. With this configuration of the anchoring members 56, the tips or ends of the second end portions 60 of the anchoring members 56 do not contact the inner wall 14 of the mammalian passageway upon deployment of the anchoring members. FIG. 6 shows the anchoring members 56 in the retracted position. FIG. 7 shows the anchoring members 56 in the deployed position. The configuration shown in FIGS. 6–7 is preferred if it is desired that no loose ends or tips of the anchoring members be in contact with the wall of the mammalian passageway upon deployment. The configuration shown in FIGS. 6–7 may also include a guide wire (not shown).

As shown in FIGS. 8–9, another variation of the anchoring members 56 and a variation of the deployment means 30 is shown. The deployment means 30 comprises a flexible, elongated, hollow tubular inner lumen 68 having a proximal end 70 and a distal end 72. A movable and flexible guide wire 74 is positioned within the inner lumen 68. The guide wire 74 has a proximal end 76 and a distal end 78. The diameter of the inner lumen 68 may be significantly smaller than the outer lumen 20 providing ease of movement of the guide wire 74 and inner lumen 68 with respect to the outer lumen 20. The distal end 78 of the guide wire 74 extends beyond the distal end 72 of the inner lumen 68 and is coupled to a cap 80. The cap 80 may be comprised of a suitable polymeric material or metal. Preferably the cap 80 is substantially cylindrical in shape. The second end portions 60 of the anchoring members 56 may also be curved inwardly toward each other and coupled to the cap element 80 via crimping, soldering or other conventional means of attachment. In use, the guide wire 74 may preferably be moved independently of the inner lumen 68 and the anchoring members 56. Upon deployment, the anchoring members 56 may or may not spring out laterally when released from the constraint of the outer lumen. However, when the guide wire 74 is pulled toward the proximal end of the outer lumen, the anchoring members 56 are pushed outwardly and the guide wire 74 adds additional bow to the shape of the anchoring members 56. FIG. 8 shows the anchoring members 56 in the retracted position. FIG. 9 shows the anchoring members 56 in the deployed position.

Once the tubular element 18 or catheter is positioned at a desired location within the passageway 12 in the mammalian body, as shown in FIGS. 1–9, the anchoring members 56 may be partially or completely reversibly deployed and retracted from an opening 82 at the distal end 26 of the outer lumen 20. The anchoring members 56 may be movable between a first position and a second position. In the first position, at least a portion of the anchoring members 56 are in a retracted position within the interior of the outer lumen 20. As shown in FIG. 1, the anchoring members 56 are shown in a retracted position and also shown in phantom in a partially deployed position. In the embodiment shown in FIGS. 1–5, the anchoring members are separate from each other, and preferably, in both the first position and the second position, the anchoring members are spaced apart from each other about the distal end of the inner lumen.

In the second position, at least a portion of the anchoring members 56 may be partially or completely deployed by the deployment means 30 exteriorly to the outer lumen 20, so that the second end portions 60 of the anchoring members 56 bow out or extend with a spring action laterally beyond the distal end opening 82 and engage the inner wall 14 of the mammalian passageway 12 and anchor or substantially anchor the tubular element 18 in a selected position within the passageway. Should a user wish to relocate the tubular element 18 to another location in the body, the anchoring members 56 may be retracted from the second position back to the first position, that is, the second end portions 60 of the anchoring members 56 may be disengaged from the inner wall 14 of the mammalian passageway 12 and may be retracted back through the distal end opening 82 of the outer lumen 20. The anchoring members 56 may be deployed over a normal distance within the mammalian passageway, or as shown in FIG. 4, the anchoring members 56 may be deployed over a very short distance, such as less than 1 centimeter, within the mammalian passageway.

Upon actuation, the deployment means 30 reversibly deploys and retracts the anchoring members 56 through the opening 82 in the distal end 26 of the outer lumen 20. The movement, deployment, and retraction of the anchoring members 56 is caused by movement of the deployment means 30 with respect to the outer lumen 20, such as by pushing the deployment means 30 forward from the proximal end 24 of the outer lumen 20 toward the distal end 26 of the outer lumen 20. Known devices may be attached to the proximal end of the deployment means to cause movement of the deployment means with respect to the outer lumen. Such known devices (not shown) may include a plunger type mechanism, a lever type mechanism, a screw type mechanism, or other suitable mechanism known in the art, that are operated by the user of the apparatus to create the reversible movement of deployment or retraction. When in the retracted position, the entire apparatus may be moved or removed to a selected location.

Figure 10:
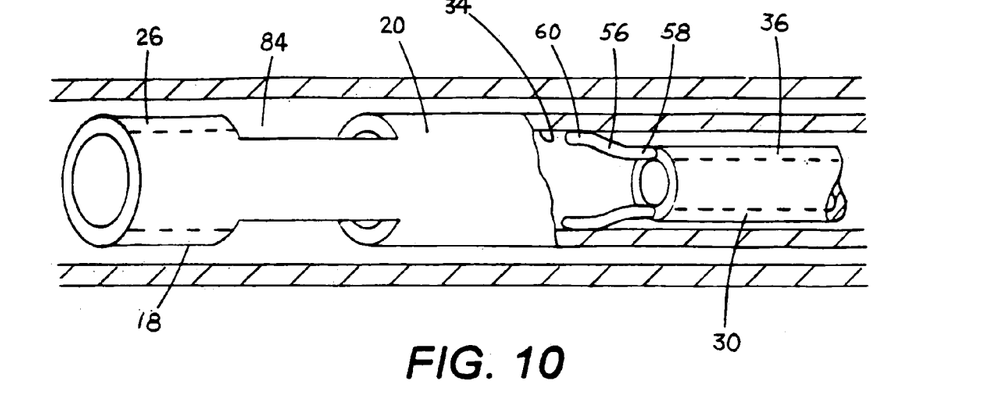
FIG. 10 shows a side view of a second embodiment of the device of the present invention positioned within a body passageway with the anchoring members in a retracted position and the outer lumen having openings.
Figure 14:
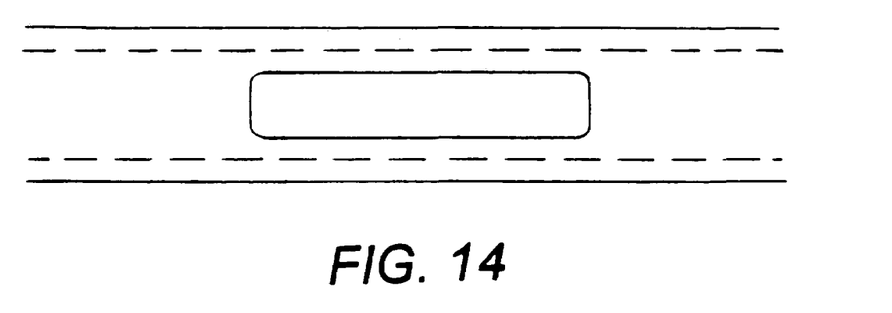
FIG. 14 shows a top view of the openings of the second embodiment of the present invention having a rectangular-shaped configuration.
Figure 15:
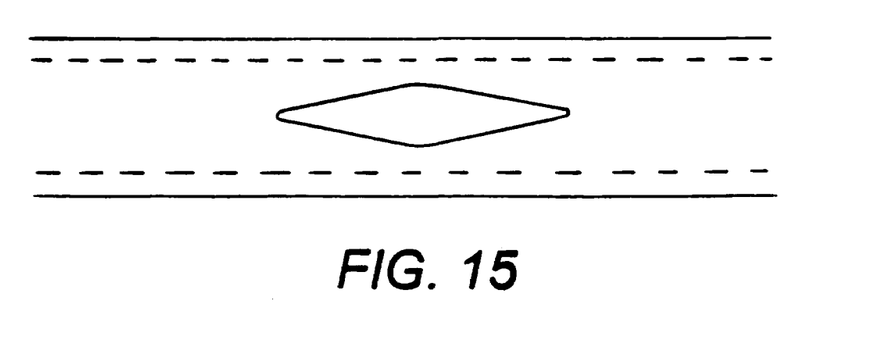
FIG. 15 shows a top of view of the openings of the second embodiment of the present invention having a diamond-shaped configuration.

FIGS. 10–13 show a second embodiment of the apparatus of the present invention. As shown in FIG. 10, the outer lumen 20 of anchoring apparatus 10 has a plurality of cut openings 84 located near the distal end 26 of the outer lumen 20. With this embodiment, the number of openings 84, should preferably correspond to the number of anchoring members 56. Preferably, the openings 84 are rectangular in shape with curved or slightly curved edges, as shown in FIG. 14, or are diamond in shape with curved or slightly curved edges, as shown in FIG. 15. Preferably, the openings 84 are spaced equidistance from each other about the circumference of the outer lumen 20. The dimensions of the openings 84 depend on the dimension of the tubular element 18 selected. However, preferably, the size of the openings 84 are in the range of about 0.5 cm (centimeter) to about 2.0 cm in length.

As shown in FIG. 10, resilient anchoring members 56 are in a retracted position within the outer lumen 20. Preferably, the anchoring members 56 in this aspect of the present invention are comprised of a pseudoelastic material or spring steel. In the retracted position, the anchoring members 56 are adjacent to the inner surface wall 34 of the outer lumen 20.

Figure 11:
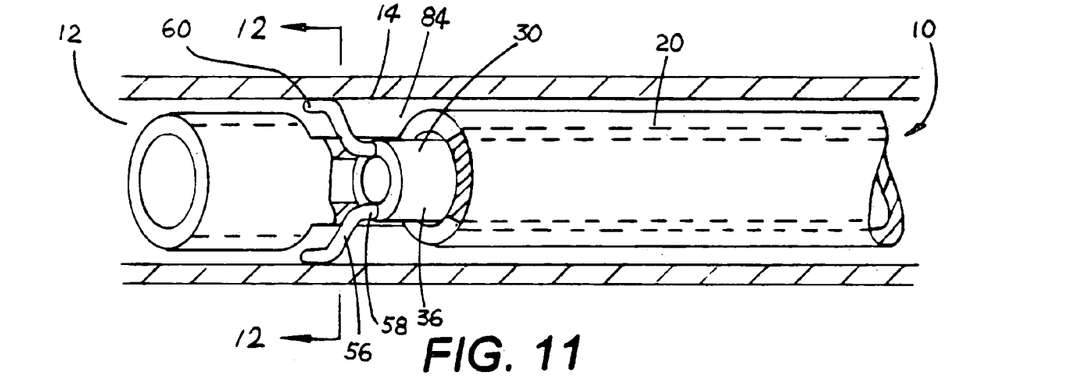
FIG. 11 shows a side view of a second embodiment of the device of the present invention positioned within a body passageway with the anchoring members in a deployed position through the openings of the outer lumen.
Figure 12:
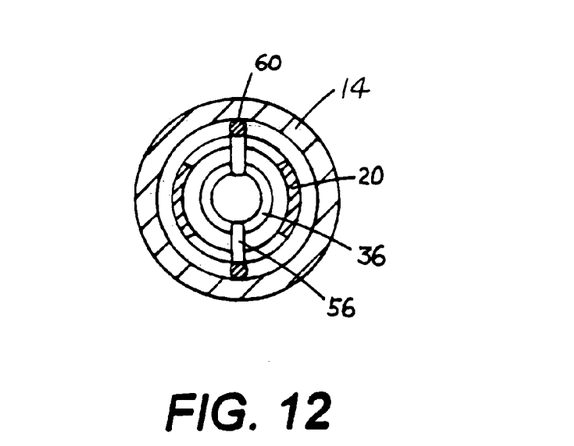
FIG. 12 shows an enlarged transverse cross-sectional view taken along lines 12—12 of FIG. 11.

As shown in FIG. 11, the anchoring members 56 are deployed by deployment means 30 through the openings 84, so that the anchoring members 56 extend with a spring action laterally through the openings 84 and engage the inner wall 14 of the mammalian passageway 12, thereby anchoring the apparatus 10 in a selected position within the passageway. Upon retraction of the anchoring members 56 by the deployment means 30, the second end portions 60 of the anchoring members 56 are disengaged from the inner wall 14 of the mammalian passageway 12 and are retracted back through the openings 84. The deployment means 30 is coupled to the first end portions 58 of the anchoring members 56 and, upon actuation, the deployment means moves the anchoring members 56 a selected distance along the outer lumen 20 and reversibly deploys and retracts the second end portions 60 of the anchoring members 56 through the openings 84. FIG. 12 shows an enlarged transversed cross-sectional view taken along lines 12—12 of FIG. 11.

Figure 13:
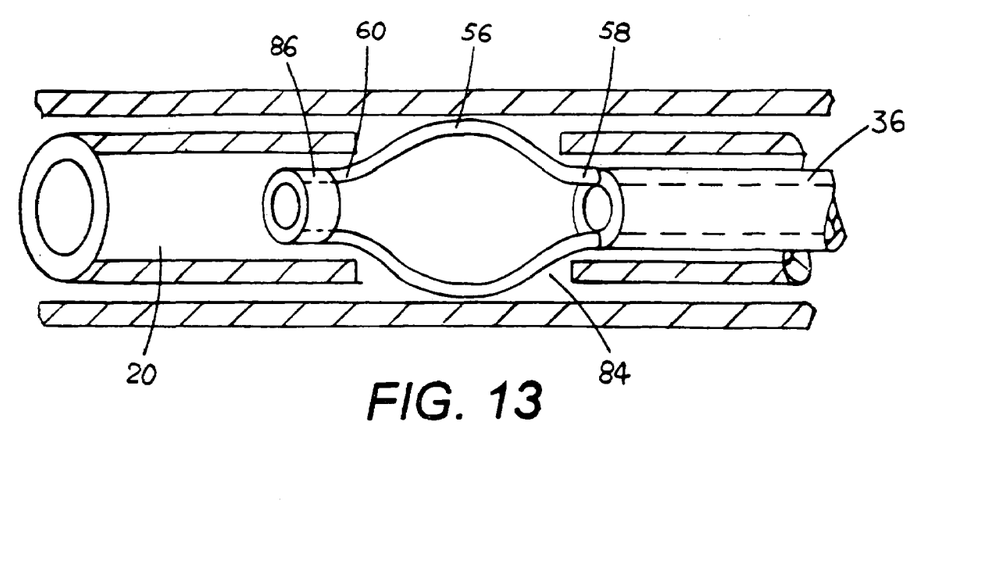
FIG. 13 shows a variation of the anchoring members of the second embodiment of the device of the present invention wherein the anchoring members are coupled to a retaining ring and at least a portion of the anchoring members are in a deployed position through the openings of the outer lumen.

As shown in FIG. 13, the anchoring members 56 may be formed in another configuration. The second end portions 60 of the anchoring members 56 may be coupled to a retaining ring 86. The retaining ring 86 may be comprised of a suitable polymeric material or a suitable metal. The retaining ring 86 is moved with movement of the inner lumen 36 and guides the anchoring members 56. With this design, when the inner lumen 36 is moved forward toward the distal end of the outer lumen 20, at least a portion of each of the anchoring members 56 extends outwardly through the openings 84 and deploy to their memory shape. The configuration shown in FIG. 13 may also include a guide wire (not shown).

The present invention also provides a method for anchoring a tubular element within a passageway formed in a mammalian body. The method comprises the steps of providing the anchoring apparatus of the present invention, positioning the apparatus at a selected location within the passageway, deploying at least a portion of the anchoring members of the apparatus against an inner wall within the passageway, and disengaging the anchoring members from the inner wall and retracting the anchoring members back into the tubular element.

Although the present invention has been described in considerable detail with reference to certain preferred embodiments thereof, other embodiments are possible. It is intended to cover all modifications, alternatives and equivalents which may fall within the spirit and scope of the invention as defined in the appended claims.

What is claimed is:

1. An apparatus for anchoring a tubular element within a passageway formed in a mammalian body, the passageway having a wall with an inner surface, the apparatus comprising:
   a) a tubular element comprising a hollow tubular outer lumen having a proximal end and a distal end;
   b) a deployment element positioned within the outer lumen and slidable with respect to the outer lumen, the deployment element comprising a hollow tubular inner lumen with a wall having an inner surface, where the inner lumen has a proximal end and a distal end, and where the inner lumen has a bore extending completely through the inner lumen from the proximal end to the distal end; and,
   c) only two resilient anchoring members attached to the distal end of the deployment element and extending longitudinally beyond the distal end of the inner lumen, each anchoring member being reversibly movable by the deployment element between a first position and a second position, where in the first position, at least a portion of each anchoring member is retracted within the outer lumen, and where in the second position, at least a portion of each anchoring member is deployed exteriorly to the outer lumen, so as to engage the inner surface of the mammalian passageway and anchor the deployment element in the passageway.

2. The apparatus of claim 1, where the tubular element is a catheter.

3. The apparatus of claim 1, where the deployment element further comprises a guide wire having a proximal end and a distal end, and where the inner lumen is a collar member attached to the distal end of the guide wire.

4. The apparatus of claim 1, where the anchoring members comprise a pseudoelastic material.

5. The apparatus of claim 4, where the pseudoelastic material is a nickel titanium alloy.

6. The apparatus of claim 1, where the anchoring members comprise spring steel.

7. The apparatus of claim 1, where the anchoring members are attached within the wall of the inner lumen.

8. The apparatus of claim 1, where the anchoring members are attached to the inner surface of the wall of the inner lumen.

9. The apparatus of claim 1, where the anchoring members are substantially oval in cross-section.

10. The apparatus of claim 1, where the anchoring members have a top portion and the top portion is substantially flat.

11. A method for anchoring a tubular element within a passageway formed in a mammalian body, the passageway having an inner surface, the method comprising:
   a) providing the apparatus of claim 1;
   b) positioning the apparatus at a selected location within the passageway; and
   c) deploying at least a portion of anchoring members against the inner surface of the passageway thereby anchoring the tubular element within the passageway at the selected location.

12. An apparatus for anchoring a tubular element within a passageway formed in a mammalian body, the passageway having a wall with an inner surface, the apparatus comprising:
   a) a tubular element comprising a hollow tubular outer lumen having a proximal end and a distal end;
   b) a deployment element positioned within the outer lumen and slidable with respect to the outer lumen, the deployment element comprising a hollow tubular inner lumen with a wall having an inner surface, where the inner lumen has a proximal end and a distal end, and where the inner lumen has a bore extending completely through the inner lumen from the proximal end to the distal end; and,
   c) only two resilient anchoring members attached within the wall of the deployment element and extending longitudinally beyond the distal end of the inner lumen, each anchoring member being reversibly movable by the deployment element between a first position and a second position, where in the first position, at least a portion of each anchoring member is retracted within the outer lumen, and where in the second position, at least a portion of each anchoring member is deployed exteriorly to the outer lumen, so as to engage the inner surface of the mammalian passageway and anchor the deployment element in the passageway.

13. The apparatus of claim 12, where the anchoring members comprise spring steel.

14. The apparatus of claim 12, where the anchoring members are substantially oval in cross-section.

15. The apparatus of claim 12, where the anchoring members have a top portion and the top portion is substantially flat.

16. The apparatus of claim 12, where the tubular element is a catheter.

17. The apparatus of claim 12, where the deployment element further comprises a guide wire having a proximal end and a distal end, and where the inner lumen is a collar member attached to the distal end of the guide wire.

18. The apparatus of claim 12, where the anchoring members comprise a pseudoelastic material.

19. The apparatus of claim 18, where the pseudoelastic material is a nickel titanium alloy.

20. A method for anchoring a tubular element within a passageway formed in a mammalian body, the passageway having an inner surface, the method comprising:
   a) providing the apparatus of claim 12;
   b) positioning the apparatus at a selected location within the passageway; and
   c) deploying at least a portion of anchoring members against the inner surface of the passageway thereby anchoring the tubular element within the passageway at the selected location.

21. An apparatus for anchoring a tubular element within a passageway formed in a mammalian body, the passageway having a wall with an inner surface, the apparatus comprising:
   a) a tubular element comprising a hollow tubular outer lumen having a proximal end and a distal end;
   b) a deployment element positioned within the outer lumen and slidable with respect to the outer lumen, the deployment element comprising a hollow tubular inner lumen with a wall having an inner surface, where the inner lumen has a proximal end and a distal end, and where the inner lumen has a bore extending completely through the inner lumen from the proximal end to the distal end; and,
   c) only two resilient anchoring members attached to the distal end of the inner wall of the development element and extending longitudinally beyond the distal end of the inner lumen, each anchoring member being reversibly movable by the deployment element between a first position and a second position, where in the first position, at least a portion of each anchoring member is retracted within the outer lumen, and where in the second position, at least a portion of each anchoring member is deployed exteriorly to the outer lumen, so as to engage the inner surface of the mammalian passageway and anchor the deployment element in the passageway.

22. The apparatus of claim 21, where the tubular element is a catheter.

23. The apparatus of claim 21, where the deployment element further comprises a guide wire having a proximal end and a distal end, and where the inner lumen is a collar member attached to the distal end of the guide wire.

24. The apparatus of claim 21, where the anchoring members comprise a pseudoelastic material.

25. The apparatus of claim 24, where the pseudoelastic material is a nickel titanium alloy.

26. The apparatus of claim 21, where the anchoring members comprise spring steel.

27. The apparatus of claim 21, where the anchoring members are substantially oval in cross-section.

28. The apparatus of claim 21, where the anchoring members have a top portion and the top portion is substantially flat.

29. A method for anchoring a tubular element within a passageway formed in a mammalian body, the passageway having an inner surface, the method comprising:
   a) providing the apparatus of claim 21;
   b) positioning the apparatus at a selected location within the passageway; and
   c) deploying at least a portion of anchoring members against the inner surface of the passageway thereby anchoring the tubular element within the passageway at the selected location.

* * * * *